(12) United States Patent
Riesinger

(10) Patent No.: US 7,922,703 B2
(45) Date of Patent: Apr. 12, 2011

(54) DRAINAGE DEVICE FOR TREATING WOUNDS USING A REDUCED PRESSURE

(76) Inventor: Birgit Riesinger, Ostbevern (DE)

( * ) Notice: Subject to any disclaimer, the term of this patent is extended or adjusted under 35 U.S.C. 154(b) by 0 days.

(21) Appl. No.: 11/791,058

(22) PCT Filed: Nov. 2, 2005

(86) PCT No.: PCT/EP2005/011702
§ 371 (c)(1), (2), (4) Date: Jul. 5, 2007

(87) PCT Pub. No.: WO2006/056294
PCT Pub. Date: Jun. 1, 2006

(65) Prior Publication Data
US 2008/0119802 A1    May 22, 2008

(30) Foreign Application Priority Data
Nov. 24, 2004 (DE) .................. 20 2004 018 245 U

(51) Int. Cl.
*A61F 13/00* (2006.01)
(52) U.S. Cl. ........................................ 604/305
(58) Field of Classification Search ............ 604/289, 604/290, 305, 306, 307, 308, 313, 315, 316
See application file for complete search history.

(56) References Cited

U.S. PATENT DOCUMENTS

| | | | |
|---|---|---|---|
| 3,111,948 A * | 11/1963 | Burgeni | 604/365 |
| 3,364,931 A | 1/1968 | Hirsch | |
| 3,871,376 A | 3/1975 | Kozak | |
| 3,872,862 A | 3/1975 | Hume | |
| 4,382,441 A | 5/1983 | Svedman | |
| 4,592,750 A * | 6/1986 | Kay | 604/337 |

(Continued)

FOREIGN PATENT DOCUMENTS

DE    195 17 699    11/1999

(Continued)

OTHER PUBLICATIONS

International Search Report (WO2008/040681 dated Feb. 19, 2008).

(Continued)

*Primary Examiner* — Tatyana Zalukaeva
*Assistant Examiner* — Ilya Y Treyger
(74) *Attorney, Agent, or Firm* — Occhiuti Rohlicek & Tsao LLP

(57) ABSTRACT

The invention relates to a drainage device (100) for the treatment of wounds using reduced pressure, comprising (a) a gas-type wound-covering element (3), which, in the state in contact with the body of the patient, is fastened cohesively at the skin surface around the region of the wound and forms a sealed wound space, remaining between the respective wound and the wound-covering element (3); (b) at least one drainage tube (4), which can be connected to means generating the reduced pressure and can be inserted into the wound space approximately parallel to the wound-covering element (3); and (c) at least one absorption body (2) in the form of at least one layer (7) of a textile section (33), which is interspersed with super-absorbing particles and enclosed in an envelope. Due to the size of the pores of the envelope, the absorbed wound secretions remain within the absorption body (2) and, with that, underneath the wound-covering element (3) until the absorption body is removed from the wound space. An air opening (34) is provided for the wound-covering element (3).

26 Claims, 9 Drawing Sheets

U.S. PATENT DOCUMENTS

| | | | |
|---|---|---|---|
| 4,969,880 A | 11/1990 | Zamierowski | |
| 5,086,763 A | 2/1992 | Hathman | |
| 5,476,664 A | 12/1995 | Robinson et al. | |
| 5,540,922 A * | 7/1996 | Fabo | 424/402 |
| 5,549,584 A | 8/1996 | Gross | |
| 5,636,643 A * | 6/1997 | Argenta et al. | 128/897 |
| 6,071,267 A * | 6/2000 | Zamierowski | 604/289 |
| 6,171,306 B1 | 1/2001 | Fleischman | |
| 6,333,093 B1 * | 12/2001 | Burrell et al. | 428/194 |
| 6,398,767 B1 * | 6/2002 | Fleischmann | 604/313 |
| 6,626,891 B2 | 9/2003 | Ohmstede | |
| 6,685,681 B2 * | 2/2004 | Lockwood et al. | 604/305 |
| 6,966,901 B2 * | 11/2005 | Leisner et al. | 604/337 |
| 7,048,706 B2 | 5/2006 | Cea | |
| 2002/0065494 A1 | 5/2002 | Lockwood et al. | |
| 2004/0030304 A1 | 2/2004 | Hunt et al. | |
| 2004/0054338 A1 | 3/2004 | Bybordi | |
| 2008/0004559 A1 | 1/2008 | Riesinger | |
| 2008/0009812 A1 | 1/2008 | Riesinger | |

FOREIGN PATENT DOCUMENTS

| | | |
|---|---|---|
| DE | 100 59 439 | 12/2005 |
| EP | 0762860 | 3/1997 |
| EP | 1 129 734 | 9/2001 |
| EP | 1177781 | 2/2002 |
| GB | 692578 | 6/1953 |
| GB | 2272645 | 5/1994 |
| WO | WO83/02054 | 6/1983 |
| WO | 96/05873 | 2/1996 |
| WO | 99/01173 | 1/1999 |
| WO | WO01/10363 | 2/2001 |
| WO | 01/89431 | 11/2001 |
| WO | 03/094813 | 11/2003 |
| WO | 2005/123170 | 12/2005 |
| WO | WO2006/048240 | 5/2006 |
| WO | WO2006/048246 | 5/2006 |
| WO | WO2008/040681 | 4/2008 |

OTHER PUBLICATIONS

International Preliminary Report on Patentability (WO2008/040681 dated Apr. 7, 2009).
International Search Report (WO2006/048240 mailed Mar. 9, 2006).
International Preliminary Report on Patentability (WO2006/048240 dated May 8, 2007).
International Search Report (WO2006/048246 dated Jun. 3, 2006).
International Preliminary Report on Patentability (WO2006/048246 dated May 22, 2007).
International Search Report (WO2006/056294 dated Apr. 10, 2006).
International Preliminary Report on Patentability (WO2006/056294 dated May 30, 2007).

* cited by examiner

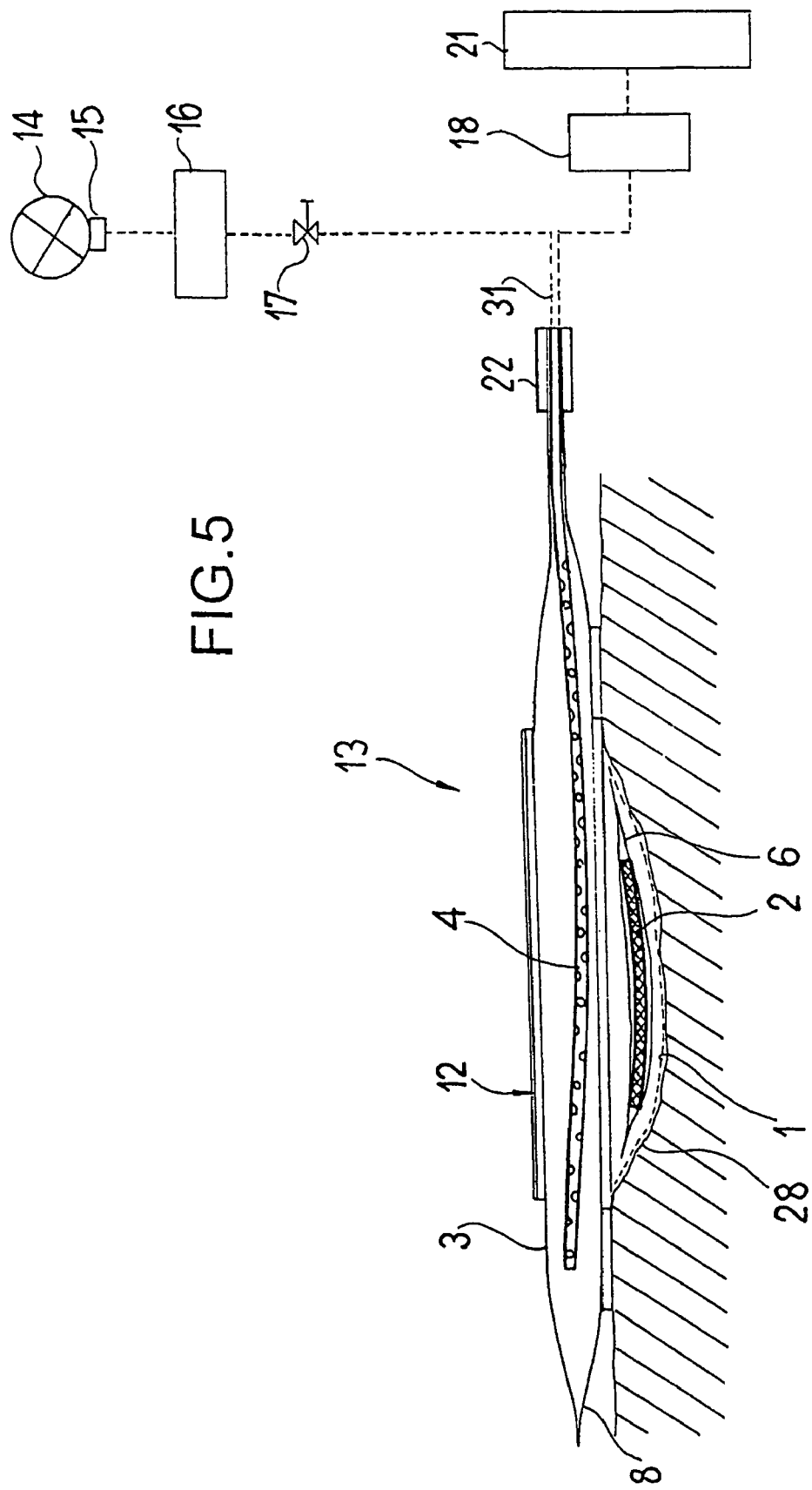

DRAINAGE DEVICE FOR TREATING WOUNDS USING A REDUCED PRESSURE

BACKGROUND OF THE INVENTION

The invention relates to a drainage device for treating wounds using a reduced pressure, comprising:
a gas-tight wound-covering element, which consists of a sheet-like material and, when placed in contact with the body of the patient, is fastened adhesively to the surface of the skin about the region of the wound, forming a sealed, wound space remaining between the respective wound and the wound-covering element, and at least one drainage tube, which can be connected to a means, such as a vacuum pump, for producing the reduced pressure and can be inserted prone into the wound space approximately parallel to the wound-covering element and over which the materials in the wound space can be evacuated,
and at least one absorption body, which is disposed in the wound space and absorbs the wound secretions.

A device of the type named above is known from the DE 195 17 699. The known device has a covering sheet for covering the wound flat and closing it off air-tight, so that a wound space, into which an insert of a foam material and a drainage hose, which is pulled into this insert, are inserted, is formed underneath the covering sheet in the region of the wound. With the help of the insert of foam material, the wound secretions are to be withdrawn uniformly over the whole of the wound surface. A collecting container with a vacuum pump for producing the reduced pressure is, in turn, connected to the drainage tube. The whole device is disposed of when the collecting container is filled with wound secretion. The purpose of the disposable device is to pass the wound secretions continuously through the drainage tube into the collecting container.

U.S. Pat. No. 5,549,584 shows a device for vacuum treatments, which consists of a wound cover, a membrane pump, which is disposed at the suction tube, and a pouch-like collector, which is connected downstream from the membrane pump. A layer of material or a loose bed of liquid-absorbing fibers, which rest on a perforated layer and under which a further adhesive layer, in turn, is placed, is disposed underneath the wound covering. Furthermore, the fibers are covered by a liquid-permeable upper layer, which has several windows. Beneath each window, there is a section of material, which is also permeable to liquids. The suction tube is connected with a connecting piece, which is disposed above the wound cover, and does not have any direct contact with the absorption material, which is located within the wound space. The device, so designed, seems complicated and expensive to produce.

The DE 29 53 373 C2 also discloses a device, which uses reduced pressure for the treatment of wounds and comprises a wound-covering element, a foam material insert underneath the wound-covering element and at least one flexible conduit, which communicates with the pores of the foam material insert. In the DE 38 50 798 T2, a sterile, rectangular, yet rigid cassette, in which a surgical dressing is accommodated, is shown. The lower edge of the cassette is fastened to the skin of the patient. For enclosing the surgical field at the patient, the cassette is open at the top and at the bottom.

U.S. Pat. No. 5,086,763 A discloses a cassette-like wound-treating device, which is also fastened to the skin of the patient. An exchangeable wound dressing is placed at the underside of a swiveling lid.

A pouch-like wound-treating and wound drainage device, known from AT E33 446 B, has a lower, peripheral edge, by which it may be glued to the skin of a patient, a catheter holder, two treatment openings with caps, which are disposed at an upper wall, as well as an opening at the lower wall of the pouch for enabling access to the wound. The publication describes only the construction of the pouch.

SUMMARY OF THE INVENTION

It is an object of the invention to design a cost-effective device for the vacuum treatment of wounds, the design of which is simplified.

This objective is accomplished by a device of the type named above, for which the absorption body is at least one textile section, in which super-absorbing particles are interspersed and which is enclosed in an envelope, the envelope being permeable to liquids and having pores, the size of which essentially does not exceed that of the super-absorbing particles, the absorption body, which is to be inserted in the wound space, having an initial volume, which enlarges in the course of the absorption process and assumes a final volume, so that the absorbed wound secretions, due to the size of the pores of the envelope, remain within the absorption body and, with that, below the wound-covering element until the absorption body is removed from the wound space.

The wound-covering element may be fastened over a flexible connecting plate, the so-called base plate, to the body of the patient. One or more openings, which are fitted to the wound area(s), are cut from the base plate before it is glued to the skin. It is, however, possible to do without the base plate, if a peripheral adhesive surface is applied, provided that the adhesive substance is harmless and an appropriate connection site for introducing the drainage hose is provided at the wound-covering element. However, a conventional commercial wound-repair pouch with a gas-tight treatment window and a drain, the side wall of which, opposite to the wound-covering element, is glued to the connection plate at the factory, is preferred.

It is important that at least one absorption body, which is enriched with super-absorbents and can be exchanged, and one drainage hose, which rests on the absorption body, are disposed within the wound-repair pouch.

The drainage tube may, however, also lie between two absorption bodies, which have the same or a different suction force and form a sandwich arrangement. For the sandwich arrangement, an absorption body, enriched with super-absorbents, and an additional absorption body, which is not provided with super-absorbents, such as a flat, open-pored foam body, may be used. Different possibilities are provided here, namely, a sandwich arrangement, for which the foam body lies between the connecting plate and the absorption body, enriched with super-absorbents, or between the wound-covering element and the absorption body, which is enriched with super-absorbents.

An optimum wound-healing process can be "programmed" by the selection of absorption bodies and their suction force.

The enveloped absorption body and/or the additional and/or the additional foam-like absorption body and/or the abhesive film element may be provided with silver-, copper- or zinc-containing substances, for example, in nano-crystalline form, in order to kill germs.

It is also important that the area of the textile section of the absorption body, enriched with super-absorbent particles, is significantly smaller that that of the envelope, so that the absorption body, without being impeded in its cross section, can approach a circular form. The full utilization of the maximum or almost maximum filling capacity of the absorption body contributes to lowering the costs of treating the wound.

The wound-covering element may be transparent at least over a portion of its surface, so that the state of the wound-healing process may be observed. The drainage device may be provided with a liquid permeable, mucous membrane compatible protective element, which is disposed on a side of the absorption body, opposite to the wound-covering element and the surface area of which is approximately equal to that of the enveloped absorption body. The protective element may also be produced from a soft, open cell foam material or a very loose nonwoven fabric. Finally, the protective element may also be a loose bed of pieces of a nonwoven material or of a foam underneath the absorption body. At the end of the absorption process, these pieces are removed from the wound, for example with forceps. Moreover, a voluminous formation fulfills not only the function of protecting the mucous membrane, but also that of an absorber. The open cell foam or the nonwoven material may have pores, which are several times larger than those of the envelope, so that the larger particles of wound exudate may be taken up.

If the device is glued to the body of the patient, the reduced pressure in the wound space beneath the wound-covering element can be produced manually or mechanically or electrically. A most simple manual production of vacuum can be brought about, for example, with the help of a so-called scissors grip vacuum pump or a known rubber bellows ("ball pump"), which can be compressed by hand. Different conventional, commercial vacuum pumps, which can be supplied, for example, together with a tube and a pressure regulator, are suitable for producing a vacuum electrically.

For an in-patient, for example, post-operative treatment of a wound, the reduced pressure can be produced by connecting the drainage device to an existing, stationary vacuum installation, optionally by way of a pressure regulator.

In a plan view of its flat side, the device may be polygonal, oval or circular or it may also be pouch-shaped, similar to the known wound-repair pouches.

The envelope consists of a liquid-permeable, mucous membrane-compatible natural material or plastic, to which the wound secretions adhere hardly, if at all. This enables liquid wound secretions to be transported into the absorption material. The wound secretions pass through the envelope and are absorbed by the absorption material, which has been enriched with super-absorbents.

Advantageously, a peripheral overhang of envelope material is provided at the envelope of the absorption body, so that any painful contact of the relative hard seam with the surface of the wound can be limited or even avoided. The envelope material a peripheral seam and the outer extent of the envelope is understood to be the overhang here.

The envelope of the absorption body many be provided with pulling means, so that the consumed, swollen absorption body can be pulled more easily out of the wound region.

The envelope, as well as the absorption material within the envelope may be provided with an odor-inhibiting and/or odor-neutralizing or odor-masking additive, such as activated charcoal.

It is of great advantage that, during the evacuation of the gases, wound secretion particles are not carried along. These remain within the envelope of the absorption body until the whole device is removed from the body of the patient and disposed of or until the swollen absorption body is exchanged. Overall, a device is created for the treatment of wounds using a reduced pressure, for which the wound secretions are aspirated by the nonwoven material of the absorption body, which is interspersed with super absorber, and remain within the envelope surrounding the absorption body without getting back from the envelope into the covered wound space. As the absorption increases, the cross sectional area of the absorption body increases greatly by a multiple and approaches a circular shape. Essentially, no wound secretions are carried along while the reduced pressure is being maintained with the help of a vacuum pump, which can be connected to the device, that is, when evacuating gases. Moreover, it is possible to do without an additional collecting container. If an excess of wound secretion is to be drained off, it is advisable to connect the drainage tube over a check valve to a collecting container, which, in turn, is connected upstream from a vacuum pump with a pressure manometer. In this case, the exchangeable absorption body acts as an intermediate storage device for the secretions emerging from the wound.

The inventive drainage device can also be used for compression therapy, for example, for the treatment of open legs.

For a full understanding of the present invention, reference should now be made to the following detailed description of the preferred embodiments of the invention as illustrated in the accompanying drawings.

BRIEF DESCRIPTION OF THE DRAWINGS

FIG. 5 shows the device of FIG. 1 or 3 in a diagrammatic longitudinal section, connected to a portable or a stationary vacuum installation.

FIG. 6b shows a section, similar to that of FIG. 6a.

DESCRIPTION OF THE PREFERRED EMBODIMENTS

Figure 1:
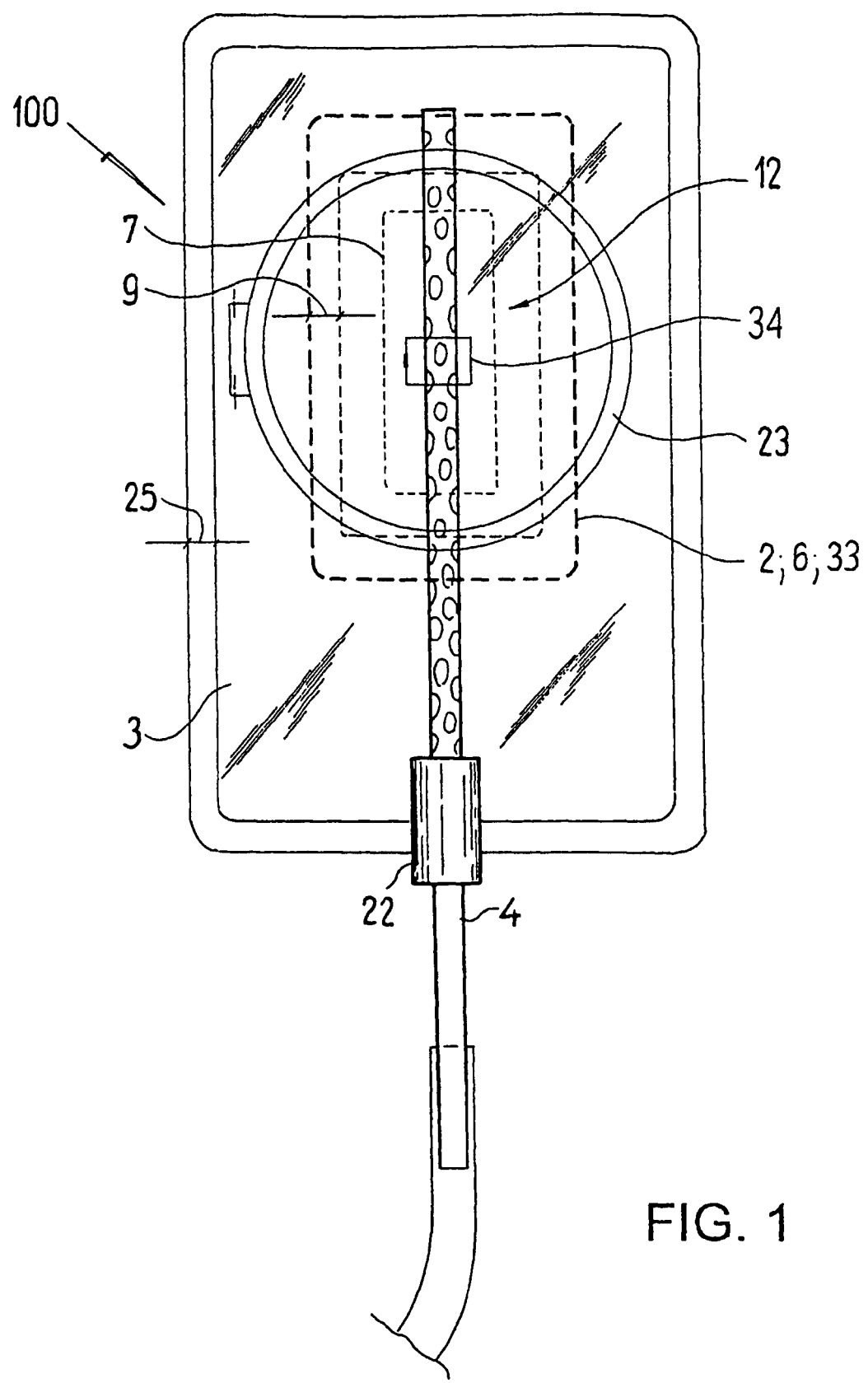
FIG. 1 shows a drainage device in plan view of the wound-covering element.

The preferred embodiments of the present invention will now be described with reference to FIGS. 1-6 of the drawings. Identical elements in the figures are designated with the same reference numerals.

FIGS. 1 and 2a to 2d show a drainage device 100 for the treatment of wounds using a reduced pressure is shown, comprising a rectangular and a sheet-like, transparent wound-covering 3, a connecting plate 10 of a hydrocolloid-like material, between which there is an absorption body 2, and a drainage tube 4. An opening 11 (compare FIG. 2a), the size of which corresponds to that of the wound, is cut out of the connecting plate 10, so that, when the device 100 is glued to the skin of the patient, a gas-tight wound space 5 results in the region of the wound (compare FIG. 2b). A peripheral edge 25 of the wound-covering element 3 is glued firmly to the connecting plate 10.

The gas-tight wound space 5 is thus bounded by the wound surface, the wound covering element 3 and the inner edge of the opening 11 at the connecting plate. This wound space has a variable volume, since the wound-covering element 3 is not tensioned. The wound space, if it is considered as a reduced pressure space, also includes the interior of the drainage tube 4 up to the obstruction element, such as the check valve 17, shown diagrammatically in FIG. 5.

The drainage tube 4 is pushed over an envelope piece 22, which is disposed at the edge of the wound-covering element 3, and under the wound covering element and rests on the absorption body 2, without contacting the wound surface.

Furthermore, at each of its two flat sides, the connecting plate 10 has a protective film 19, 24, of which the protective film 19, facing the later wound region, can be pulled off. The other protective film 24 is finished to be adhesive on the side facing the wound-covering element 3.

The absorption body 2 is a layer 7 (compare FIG. 2a) of a textile section 33, which is enriched with super-absorbents and surrounded by the liquid-permeable envelope 6. The envelope 6 has a peripheral overhang 9 of material at its periphery, the area of the layer 7 being about 40% smaller than that of the envelope 11.

A drainage device 200, similar to the one described above, is sharing in FIGS. 3 and 5. For this drainage device 200, the wound covering element 3 is part of a known wound-repair pouch 13 with a neck 27, the side wall 8 (compare FIG. 5) of which, opposite the wound-covering element 3, is glued rigidly to the hydrocolloidal connecting plate 10, an outline 26 of the wound-repair pouch, placed flat, protruding beyond the connecting plate. The flat absorption body 2 is accommodated in the interior of the wound-repair pouch 13, which is glued to the skin of the patient. The wound contour 28 is outlined with a line 28 of dashes.

Figure 3:
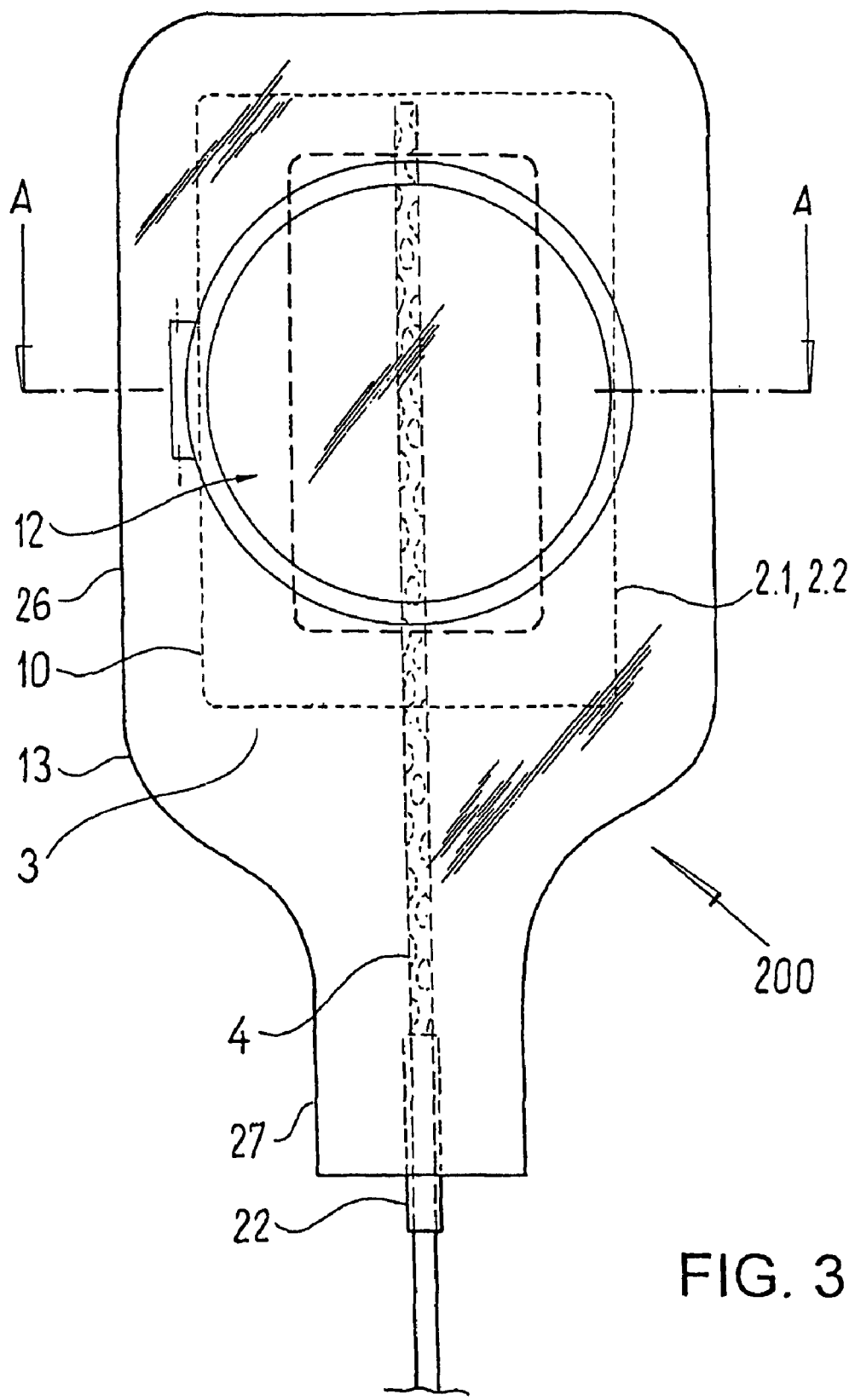
FIG. 3 shows the device of FIG. 1, however with a neck, also in plan view of its flat side.
Figure 4A:
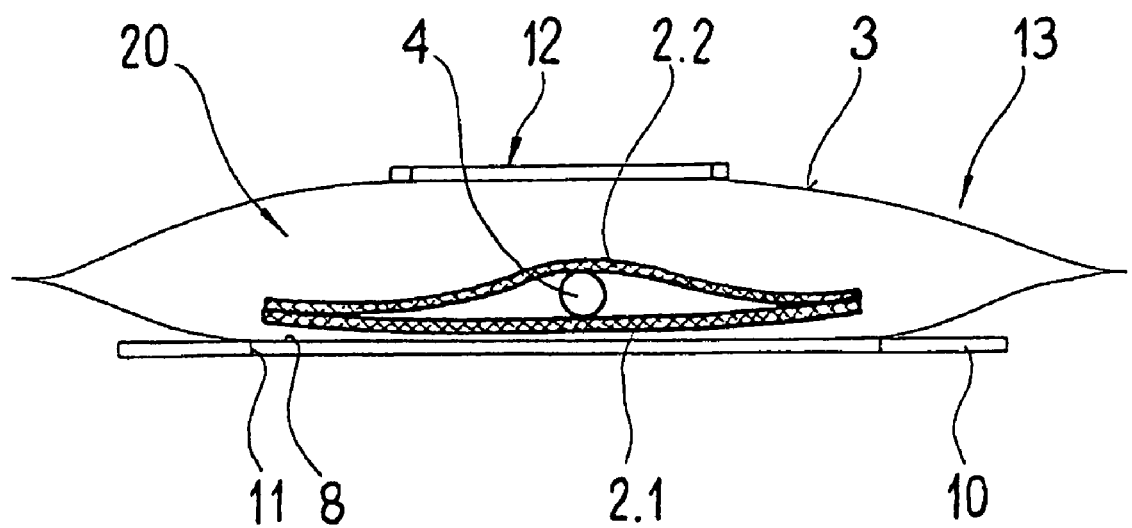
FIGS. 4a to 4c show a section A-A of FIG. 3 with three different sandwich arrangements of two absorption bodies.
Figure 4B:
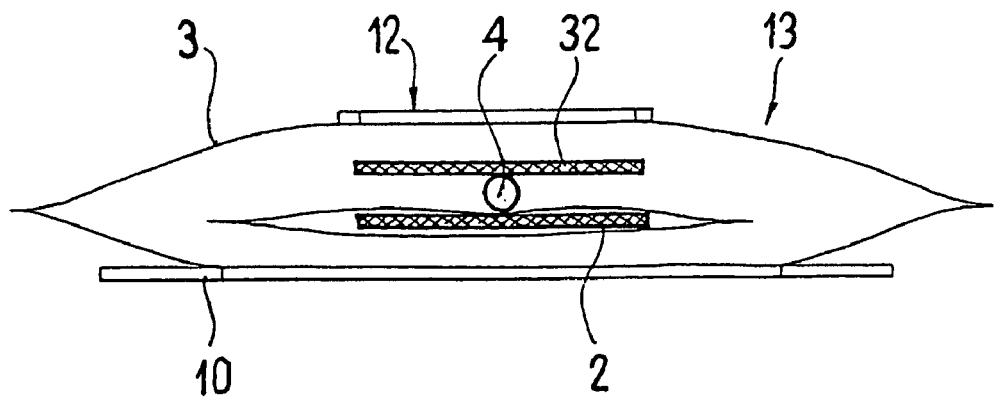

FIG. 4a shows the drainage device 200 in the section A-A of FIG. 3. A sandwich arrangement 20 of two absorption bodies 2.1, 2.2, between which the drainage tube 4 is located, is a special feature of this embodiment. FIG. 4b also shows a sandwich arrangement, for which an additional absorption body 32, which is not provided with super-absorbents, is located between the wound-covering element 3 and the absorption body 2, which is enriched with super-absorbents. In FIG. 4c, once again a sandwich arrangement is shown, for which the additional absorption body 32 is located between the connecting plate 10 and the absorption body 2, which is enriched with super-absorbents. In the last two cases, the drainage tube 4 is disposed between the absorption bodies 2; 32, which differ from one another. The additional super-absorber-free absorption body 32 is present in the form of an open pore foam body.

Figure 6A:
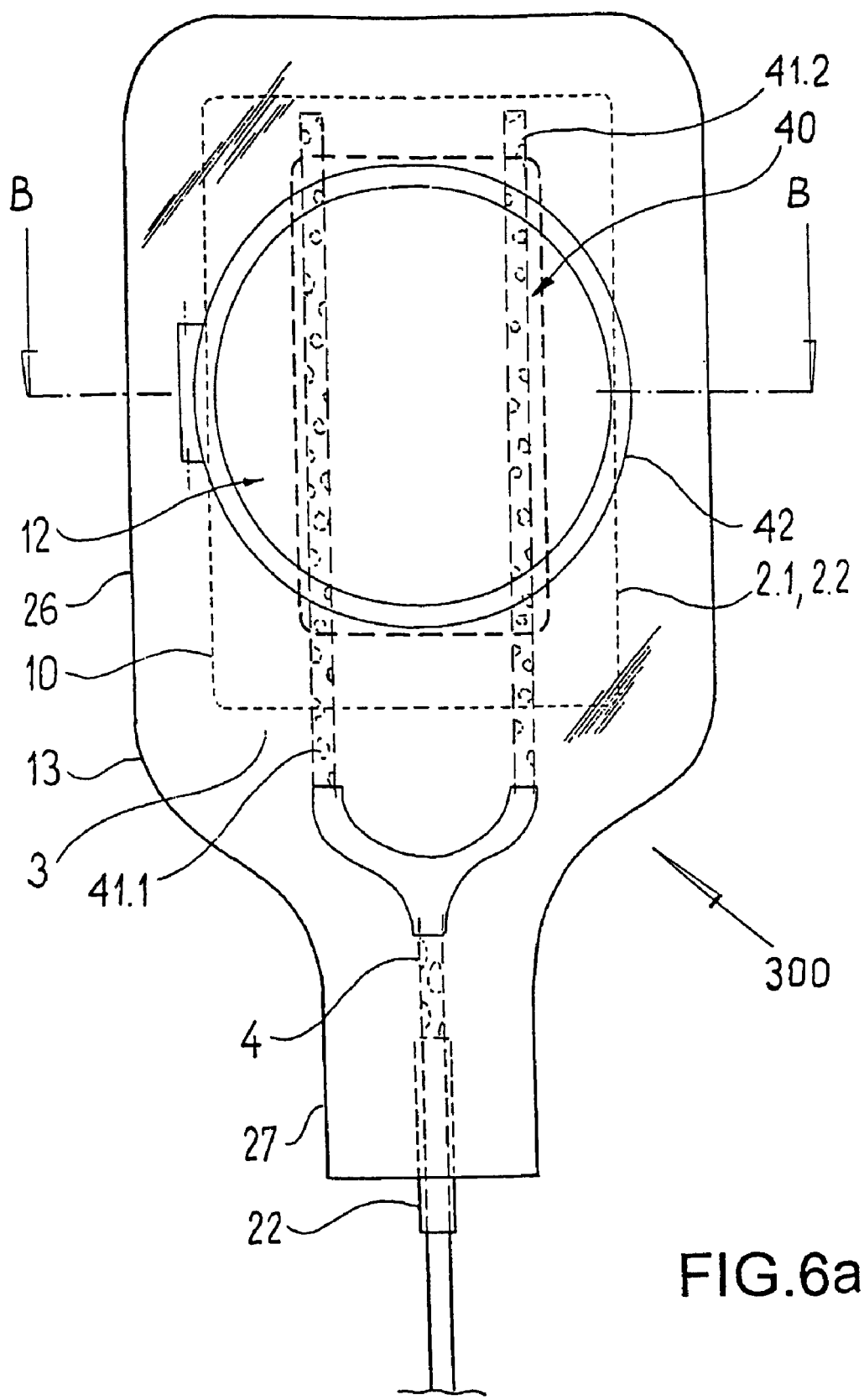
FIG. 6a shows a further embodiment of the drainage device in plan view of the wound-covering element.
Figure 6B:
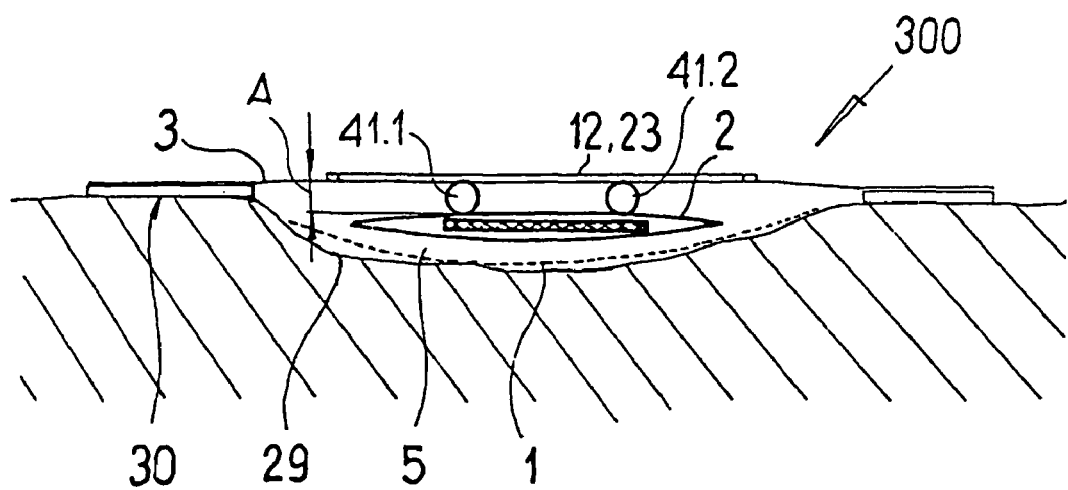

A relatively wide, round treatment opening 12, through which the absorption body 2 or the additional absorption body 32 can be placed in or removed from the wound space 5, is incorporated at the wound covering element 3. The treatment opening 12 can be closed off gas-tied with a swiveling lid 23. An air opening 34, which is disposed in the center of the swiveling lid 23 and with which the reduced pressure can be regulated and adjusted in such a manner, that there may be a draft of air within the wound space during the suction process, is shown diagrammatically in FIG. 1. FIGS. 6a and 6b show a drainage device 300, which is essentially similar to that shown in FIG. 1. The difference consists therein that the perforated part of the drainage tube 4 underneath the wound-covering element 3 is forked. A stable pressure distributor 40 results in this way, since the two branches 41.1, 41.2 rest on the absorption body 2 and press against a reinforced rim 42 of the swiveling lid 23.

Figure 4C:
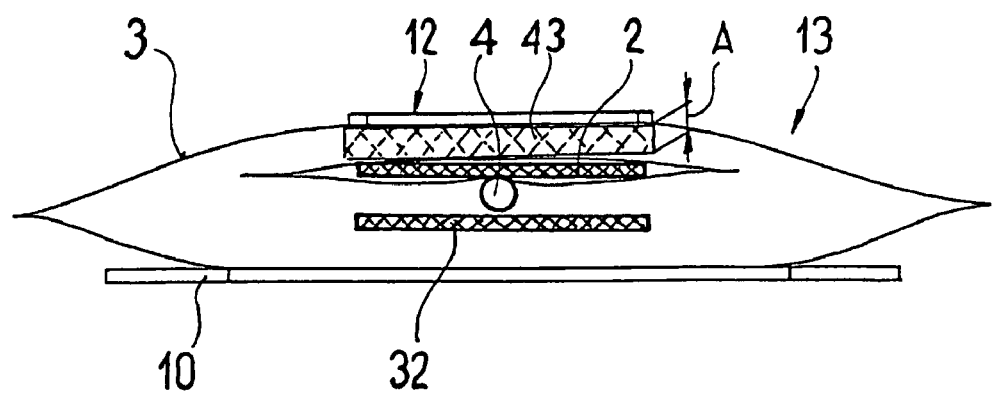

A different pressure distributor 43 is present in the form of a flat, open cell foam piece 44 (compare FIG. 4c). The foam piece 44 is hardly compressible and therefore retains its thickness, which defines a required distance A between the wound-covering element 3 and the absorption body 2.

In addition, a sterile, air-tight packaging (not shown) is provided for the device.

Function (see FIGS. 2a to 2d and 5):

A deep wound 29 is covered completely by gluing the drainage device (100) of FIG. 1 to the skin of the patient. Previously, an opening 11 was cut out of the connecting plate 10 and, after that, the protective film 19, shown in FIG. 2a, was removed, so that an adhesive surface 30 at the underside of the connecting plate 10 is exposed.

To begin with, the mucous membrane-compatible, perforated, film-like protective element 1 and then the flat absorption body 2 together with the envelope 6 were carefully placed through the treatment opening 12 with sterilized forceps (not shown) onto the surface of the wound. The absorption body 2 has an initial volume V1. The drainage tube 4 is then pushed in over the envelope piece 22 and under the wound covering element 3 in such a manner that it rests on the envelope of the absorption body 2 (see FIG. 2b). By gluing the drainage device to the skin, a gas-tight wound space 5 is formed between the wound-covering element 3 and the surface of the wound.

Figure 2A:
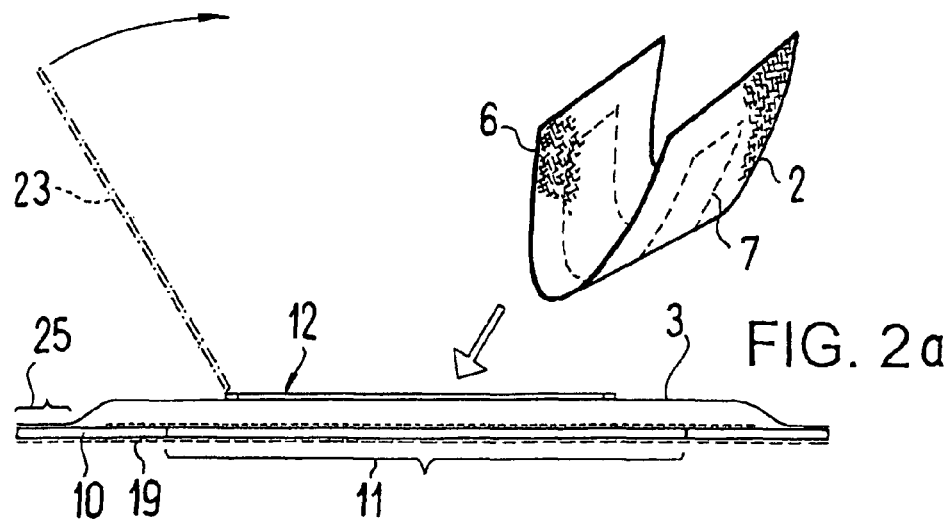
FIGS. 2a to 2d show the device of FIG. 1, glued to the skin of the patient, in a diagrammatic section.
Figure 2B:
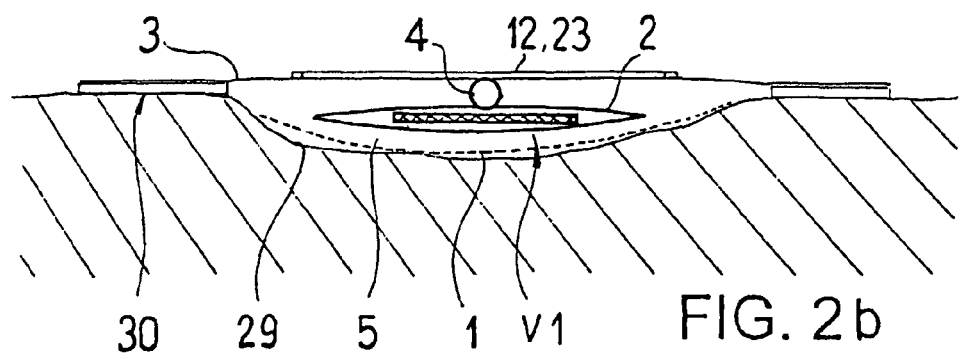
Figure 2C:
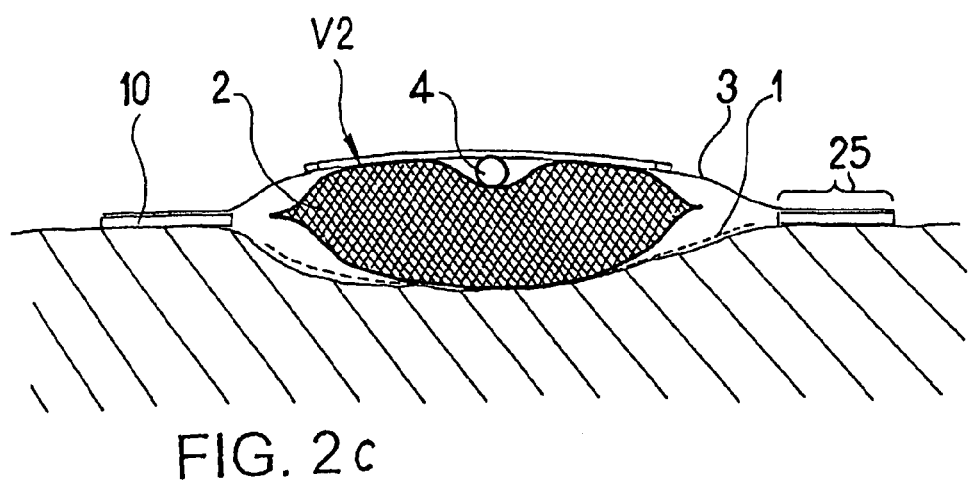

A vacuum pump 15, which can be operated by hand and is equipped with a pressure manometer 15 (see FIG. 5), is connected over a line 31 with the drainage tube 4. Since the wound space 5 is sealed, the gases in the wound space 5 can be evacuated with the help of the vacuum pump 15. The state is shown in FIGS. 2b and 5. A reduced pressure of about 100 mm Hg was produced within the wound space 5 with the help of the vacuum pump 15. A check valve 17, which permits the flow of gases and possibly of liquid wound secretions only in the direction of a collection container 16, which is connected upstream from the vacuum pump 16, is disposed in the line 31 between the envelope piece 22 and the vacuum pump 14.

The wound secretions, emerging from the wound, reach the absorption body 2 and bring about a compression underneath the wound-covering element 3. After the aspiration of wound secretions, the absorption body 2 assumes a final volume V2 (see FIGS. 2c and 2d). All wound secretions, which have emerged from the wound, are absorbed by the absorption body 2. Basically, the outside of the envelope 6 remains dry.

Figure 2D:
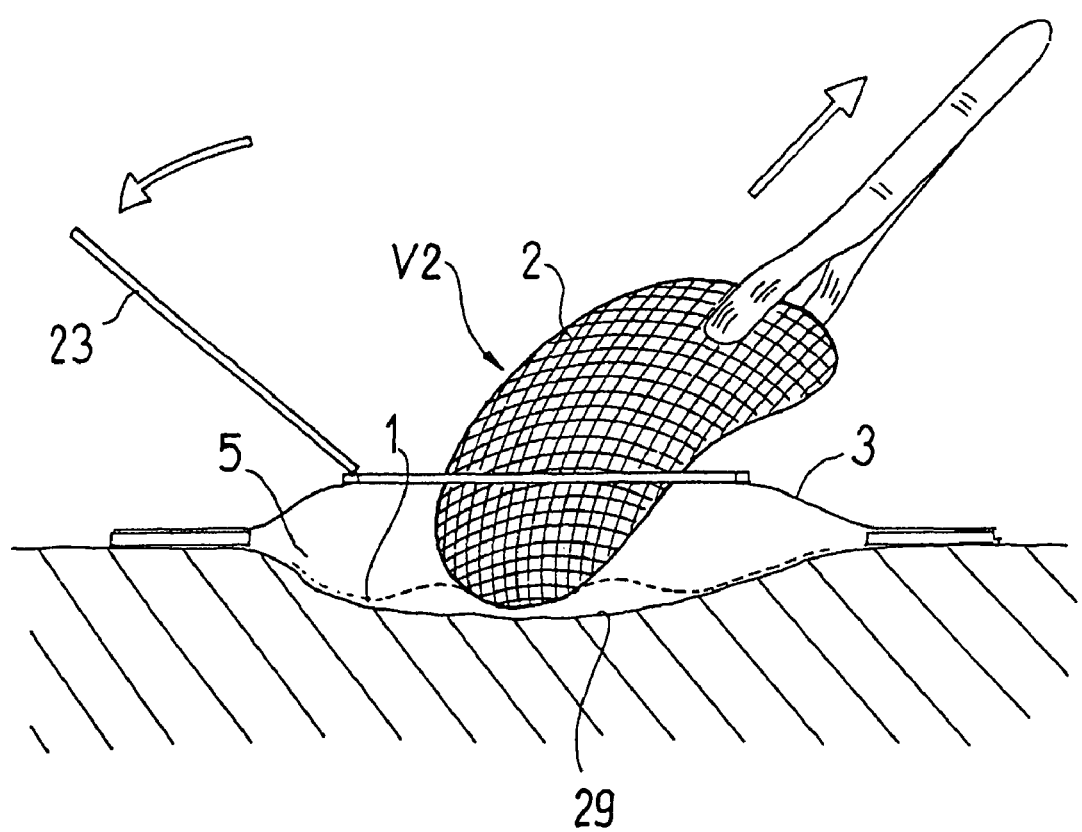

The consumed absorption body 2 and the protective element 1 are now removed carefully from the region of the wound by raising the pivoting lid 23 with the help of forceps (see FIG. 2d). If required, a new absorption body and a new protective element 1 can be placed on the wound. If the wounds discharge very heavily, there may be an excess of wound secretion, which is passed over the drainage tube 4 to the collecting container 16.

If the patient is to be subjected to an in-patient wound treatment, the reduced pressure can be produced in the wound space in the wound region by an existing, clinical vacuum installation 21 (FIG. 5). For this purpose, it is advisable to incorporate a pressure regulator 18, with which the reduced pressure range can be adjusted, in the line between the drainage tube 4 and the vacuum installation 21.

There has thus been shown and described a novel drainage device for treating wounds using a reduced pressure which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. Drainage device for the treatment of wounds using reduced pressure, comprising:
   (a) a gas-tight wound-covering element, which comprises a sheet-like material and, in the state placed in contact with the body of the patient, is fastened adhesively to the surface of the skin around the region of the wound and forms a sealed wound space between the respective wound and the wound-covering element,
   (b) at least one means for producing a reduced pressure, connected to a drainage tube, which can be inserted into the wound space approximately parallel to the wound-covering element, by means of which material in the wound space can be evacuated, and
   (c) at least one absorption body, which is disposed in the wound space and absorbs the wound secretions,
   wherein
   the absorption body has at least one layer, which is enclosed in an envelope, of a textile section interspersed with super-absorbing particles, the envelope being permeable to liquids and having pores, the size of which essentially does not exceed that of the super-absorbing particles,
   the absorption body, which is to be inserted in the wound space, has an initial volume ($V1$), which increases in the course of the absorption process and assumes a final volume ($V2$), so that, due to the pore size of the envelope, the absorbed wound secretions remain within the absorption body and, with that, underneath the wound-covering element until the absorption body is removed from the wound space, and
   the wound-covering element has
      a window-like treatment opening, through which the absorption body can be placed into and removed out of the wound space, and a gas-tight lid configured to close off the treatment opening, and
      at least one air opening, with which the reduced pressure within the wound space can be regulated, disposed in the lid.

2. The drainage device of claim 1, wherein, in plan view of its flat side, the layer has an area, which is 3% to 90% smaller than that of the envelope, so that the absorption body can unimpededly approach a circular shape in cross section in the vicinity of its total filling capacity.

3. The drainage device of claim 1, wherein the textile section of the absorption body comprises a non-woven material of cellulose fibers.

4. The drainage device of claim 1, further comprising a liquid-permeable mucous membrane-compatible protective element, which is disposed on a side of the absorption body, opposite to the wound covering element and is approximately equal in area to the enveloped absorption body.

5. The device of claim 4, wherein the protective element is in the form of a sheet.

6. The device of claim 4, wherein the protective element is a section of textile material.

7. The device of claim 4, wherein the protective element consists of a foam material.

8. The device of claim 4, wherein the protective element is a bed of pieces of nonwoven material or of foam, lying underneath the absorption body.

9. The drainage device of claim 1, wherein the wound-covering element is transparent at least at a portion of its surface.

10. The drainage device of claim 1, wherein the wound-covering element is fastened over a flexible connecting plate to the body of the patient, at least one opening being incorporated in the flexible connecting plate.

11. The drainage device of claim 10, wherein the wound-covering element is part of a medical care pouch, the side wall of which, lying opposite the wound-covering element, is affixed at least partly to the connecting plate.

12. The drainage device of claim 1, wherein the envelope of the absorption body is sealed by ultrasonic seams.

13. The drainage device of claim 1, wherein the absorption body has an overhang of enveloping material at its periphery.

14. The drainage device of claim 1, wherein the drainage tube is passed to a collecting container, which is connected upstream from a vacuum pump and a pressure manometer.

15. The drainage device of claim 14, wherein the vacuum pump is driven by at least one of electrical and mechanical means.

16. The drainage device of claim 1, wherein the drainage tube lies between two absorption bodies forming a sandwich arrangement.

17. The drainage device of claim 16, wherein the sandwich arrangement has an absorption body, which is interspersed with super-absorbents, and at least one additional absorption body which is not provided with super-absorbents.

18. The drainage device of claim 17, wherein the additional absorption body is an open pore foam body.

19. The drainage device of claim 17, wherein the additional absorption body lies between the connecting plate and the absorption body, which is interspersed with super-absorbents.

20. The drainage device of claim 17, wherein the additional absorption body lies between the wound-covering element and the absorption body, which is interspersed with super absorbents.

21. The drainage device of claim 18, wherein the absorption body, the additional foam-like absorption body and the protective element have at least one of silver-containing, copper-containing and zinc-containing substances.

22. The drainage device of claim 21, wherein the absorption body, the additional foam-like absorption body and the protective element is enriched with activated charcoal.

23. The device of claim 1, further comprising a pressure distributor, contacting the envelope of the absorption body, disposed underneath the wound-covering element, but above at least one of the enveloped absorption body and the additional foam-like absorption body.

24. The device of claim 23, wherein the pressure distributor is a piece molded from a gas-permeable foam.

25. The device of claim 23, wherein the pressure distributer is formed by the drainage tube extending in forked, loop-like or meandering fashion underneath the wound-covering element.

26. The drainage device of claim 1, wherein the drainage device is connected over a pressure regulator to an existing, stationary, clinical vacuum installation.

* * * * *